United States Patent [19]

Watanabe

[11] Patent Number: 4,545,681

[45] Date of Patent: Oct. 8, 1985

[54] METHOD AND APPARATUS FOR CONTROLLING MEASUREMENT IN A SPECTROPHOTOMETER

[75] Inventor: Shinichiro Watanabe, Tokyo, Japan

[73] Assignee: Japan Spectroscopic Co., Ltd., Hachioji, Japan

[21] Appl. No.: 465,337

[22] Filed: Feb. 9, 1983

[30] Foreign Application Priority Data

Feb. 14, 1982 [JP] Japan .................................. 57-22478

[51] Int. Cl.⁴ .............................................. G01J 3/42
[52] U.S. Cl. ................................................... 356/325
[58] Field of Search ............... 356/319, 323, 324, 325

[56] References Cited

U.S. PATENT DOCUMENTS 4,180,327 12/1979 Maeda et al. ................... 356/325 X
4,305,664 12/1981 Akitomo ............................. 356/323

Primary Examiner—F. L. Evans
Attorney, Agent, or Firm—Wenderoth, Lind & Ponack

[57] ABSTRACT

In a spectrophotometer of double beam type using automatic gain control, preparatory scanning is first carried out by scanning reference and sample cells with radiation of varying wavelengths both in an empty state, and controlling the gain of a photo detector at each wavelength such that a detector output responding to a sample cell transmitted beam may become constant while storing a detector output responding to a reference cell transmitted beam. Measurement of a sample material is then carried out at each wavelength by scanning the reference cell and the sample material-charged sample cell, reading out the reference output stored in the preparatory scanning stage as a reference voltage, and controlling the gain of the detector such that a detector output responding to a reference cell transmitted beam may be equal to the reference voltage.

11 Claims, 8 Drawing Figures

METHOD AND APPARATUS FOR CONTROLLING MEASUREMENT IN A SPECTROPHOTOMETER

BACKGROUND OF THE INVENTION

This invention relates to spectrophotometers, and more particularly, to a method and apparatus for controlling measurements in a spectrophotometer of the type wherein monochromatic radiation of varying wavelengths is alternately directed to a reference cell and a sample cell containing a sample to be analyzed so as to form reference and sample beams which are received by a radiation detector which in turn, produces corresponding electrical outputs; an output of the detector responding to the sample beam is compared with that of the detector responding to the reference beam, and the difference between these outputs is derived as the transmittance of the sample.

Among such conventional spectrophotometers, are known spectrophotometers of so-called dynode feedback system using a photodetector in the form of a photomultiplier whose gain is automatically controlled such that outputs of the multiplier which responds to radiation transmitted through a reference cell may be constant at all wavelengths at which measurements are made. One example of these prior art spectrophotometers is shown in FIG. 6.

Referring to FIG. 6, there is illustrated at 1 a main section of a prior art spectrophotometer which includes a radiation source 2 capable of emitting monochromatic radiation of varying wavelengths, for example, a monochromator, a sample chamber or cell 3 containing a sample to be analyzed, a reference chamber or cell 4 to be described later, a photo detector in the form of a photomultiplier 5, and beam path switching means 6 for causing monochromatic radiation from the source 2 to alternately enter the sample cell 3 and the reference cell 4 to form sample and reference beams and directing in synchronism the sample and reference beams from the sample and reference cells 3 and 4 alternately to the photomultiplier 5. The reference cell 4 is used in the state that its transmittance is substantially 100% and it shows no characteristic wavelength response, that is, in an empty state (an empty cell is placed in the beam path) or in the state that the cell is charged with a standard material having a flat wavelength response and a high transparency. The beam path switching means 6 includes an inlet beam path switching device 7 called a sector adapted to be rotated by means of a motor (not shown) so as to alternately switch the radiation from the source 2 to the sample cell 3 and the reference cell 4 so as to form sample and reference beams, and an outlet beam path switching device 8 adapted to be rotated in synchronism with the inlet beam path switching device 7 so as to alternately direct the sample and reference beams to the photomultiplier 5. The beam paths extending from the inlet beam path switching device 7 to the outlet beam path switching device 8 through the sample and reference cells 3 and 4 are referred to as "sample path" and "reference path", respectively, in this specification. An output of the photomultiplier 5 is supplied to a sample/hold circuit 9 and an error control circuit 10 through an amplifier 11 as will be described in more detail.

The photomultiplier 5 or the amplifier 11 produces output signals S as shown in FIG. 7(A). In FIG. 7(A), a represents an impulse corresponding to the reference beam, i.e. -the beam transmitted through the reference cell 4, and b represents an impulse corresponding to the sample beam, i.e -the beam transmitted through the sample cell 3. A low level portion c between these impulses a and b corresponds to background radiation during the beam path switching and including dark current. The sample/hold circuit 9 is designed to effect sampling in synchronism with a timing pulse TA developed in the duration when the beam path switching means 6 is switched to provide the sample path, that is, the duration of an impulse b as shown in FIG. 7(B). The sample/hold circuit 9 thus produces an output corresponding to the level of an impulse b among output signals S of the amplifier 11, that is, an output corresponding to the intensity of the same beam. Further, the error control circuit 10 functions to derive a signal corresponding to the intensity of the reference beam among output signals S of the amplifier 11, compare it with a reference voltage to determine the difference between them, and control the sensitivity of the photomultiplier 5 in accordance with said difference in a feedback manner such that the impulses a representative of the reference beam intensity among output signals S of the amplifier 11 may be kept at a constant level. In the illustrated example, the error control circuit 10 consists of a circuit 10A for generating a reference voltage and a synchronization error integrator 10B adapted to operate in synchronism with a timing pulse TB developed in the duration when the beam path switching means 6 is switched to provide the reference path, that is, the duration of an impulse a as shown in Fig.7(C), for reading out the level of the impulse a and integrating the difference between said level and the reference voltage. Since the synchronization error integrator 10B is electrically connected to a high voltage source 12 which drives the photomultiplier 5, the output voltage of the source 12 is controlled by the output of the integrator 10B.

Since the detection system of the spectrophotometer shown in FIG. 6 is controlled such that impulses a among output signals S of the amplifier 11, that is, outputs of the detector which responds to the reference beam are kept at a constant level at all wavelengths, the output of the sample/hold circuit 9 not only corresponds to the intensity of the sample beam, but also directly represents the ratio of the intensity of the sample beam to the intensity of the reference beam at any wavelength, that is, the transmittance of the sample material itself at any wavelength.

In the above-mentioned feedback control system, in order that an output of the sample/hold circuit 9 precisely represents the transmittance of a sample itself at any wavelength, it must be satisfied that the sample and reference paths in the spectrophotometer main section have precisely identical wavelength response. However, even when the sample and reference paths are made identical in wavelength response in the stage of design and fabrication, they tend to show a difference in wavelength response due to staining and fogging of mirrors in both the beam paths as measurements are repeated. In such a case, an output of the sample/hold circuit 9 cannot accurately represent the transmittance of a sample itself at some wavelengths at which the sample and reference paths differ in wavelength response. Differently stated, in such a case, when scanning is carried out at each wavelength with the sample cell 3 emptied or set to 100% transmittance, outputs of the sample/hold circuit 9 show fluctuations with respect to the given level. Then, when measurement is made at each wavelength with the sample cell 3 charged with a sample material, an output of the sample/hold circuit 9 will not correctly represent the transmittance of the sample material.

One approach to solve this problem is that the operator manually operates a voltage regulator or other control such that outputs of the sample/hold circuit 9 may become constant when scanning is made at varying wavelengths with the sample cell 3 emptied or set to 100% transmittance. In fact, such manual adjustment is impractical because of complicatedness and inaccuracy.

It is, therefore, an object of the present invention to provide a method and apparatus for automatically controlling measurement in a spectrophotometer such that even when the sample and reference paths are not precisely identical in spectral response, an output of a detector which responds to a sample beam may correctly represent the transmittance of the sample at any wavelength.

SUMMARY OF THE INVENTION

The present invention is directed to a spectrophotometer of the double beam type wherein monochromatic radiation of varying wavelengths is alternately directed to a reference cell having a transmittance of substantially 100% and a sample cell containing a sample to be analyzed so as to form reference and sample beams the reference beam and the sample beam are detected for each wavelength by means of a radiation detector which produces an electrical output, and an output of said detector which responds to the reference beam is fed back to said detector such that said output may be equal to a reference voltage upon measurement of the sample at all wavelengths, thereby controlling the sensitivity of said detector or the gain of an amplifier connected to said detector, whereby an output of said detector which responds to the sample beam represents the transmittance of the sample for each wavelength. According to a first aspect of the invention, there is provided a method for controlling the measurement in the aforementioned spectrophotometer, comprising (a) a preparatory scanning stage including setting both the reference and sample cells to a substantially 100% transmittance state; scanning the reference and sample cells with radiation of each wavelength at which measurement is to be made in said state; feeding back an output of the detector which responds to the sample beam during said scanning to said detector such that said detector output responding the sample beam may become constant at all wavelengths, thereby controlling the sensitivity of said detector or the gain of said amplifier; and storing an output of said detector which responds to the reference beam during said scanning; and (b) a sample analyzing stage in which using the stored output for each wavelength of said detector which has responded to the reference beam during said preparatory scanning or the corresponding voltage as a reference voltage, said detector is controlled upon measurement of the sample such that an output of said detector which responds to the reference beam may be equal to said reference voltage.

According to a second aspect of the invention, there is provided a method for controlling the measurement in the aforementioned spectrophotometer, comprising (a) a preparatory scanning stage including setting both the reference and sample cells to a substantially 100% transmittance state; scanning the reference and sample cells with radiation of each wavelength at which measurement is to be made in said state; feeding back an output of the detector which responds to the reference beam during said scanning to said detector such that said output may become constant at all wavelength, thereby controlling the sensitivity of said detector or the gain of an amplifier connected to the detector; and storing an output of said detector which responds to the sample beam during said scanning or its reciprocal, and (b) a sample analyzing stage including multiplying the reciprocal of the output stored for each wavelength of said detector which has responded to the sample beam during said preparatory scanning by a standard voltage to form a reference voltage; and controlling said detector upon measurement of the sample such that an output of said detector which responds to the reference beam may be equal to said reference voltage.

According to a third aspect of the invention, there is provided an apparatus for controlling the measurement in a spectrophotometer of the double beam type comprising a radiation source capable of emitting monochromatic radiation of varying wavelengths, a reference cell, a sample cell, a radiation detector which produces an electrical output, and a beam path switching means for directing monochromatic radiation of varying wavelengths from the source alternately to the reference and sample cells to form reference and sample beams and directing in synchronism the reference and sample beams to said detector. The control apparatus is characterized by comprising (a) a sample/hold circuit for sampling an output of said detector in synchronism with a first timing signal, (b) a computer having a function of storing an output of said sample/hold circuit and reading out the data stored, (c) a reference voltage generating circuit for generating a reference voltage corresponding to the output signal of said sample/hold circuit previously stored in said computer, (d) an error control circuit for comparing the output of said detector with the reference voltage in synchronism with a second timing signal and controlling in accordance with the difference, the sensitivity of said detector or the gain of an amplifier connected to said detector for amplifying an output signal thereof, and (e) a sync signal generating circuit for generating said first and second timing signals in response to the switching of said beam path switching means, wherein said sync signal generating circuit is switched between (1) a first state in which said circuit generates as the first timing signal a signal within a duration when said detector is producing an output by detecting the reference beam, and as the second timing signal a signal within a duration when said detector is producing an output by detecting the sample beam, and (2) a second state in which said circuit generates as the first timing signal a signal within a duration when said detector is producing an output by detecting the sample beam, and as the second timing signal a signal within a duration when said detector is producing an output by detecting the reference beam.

BRIEF DESCRIPTION OF THE DRAWINGS

The invention will be more fully understood by reading the following description of preferred embodiments when taken in conjunction with the accompanying drawings, in which.

DETAILED DESCRIPTION OF THE INVENTION

Figure 1:
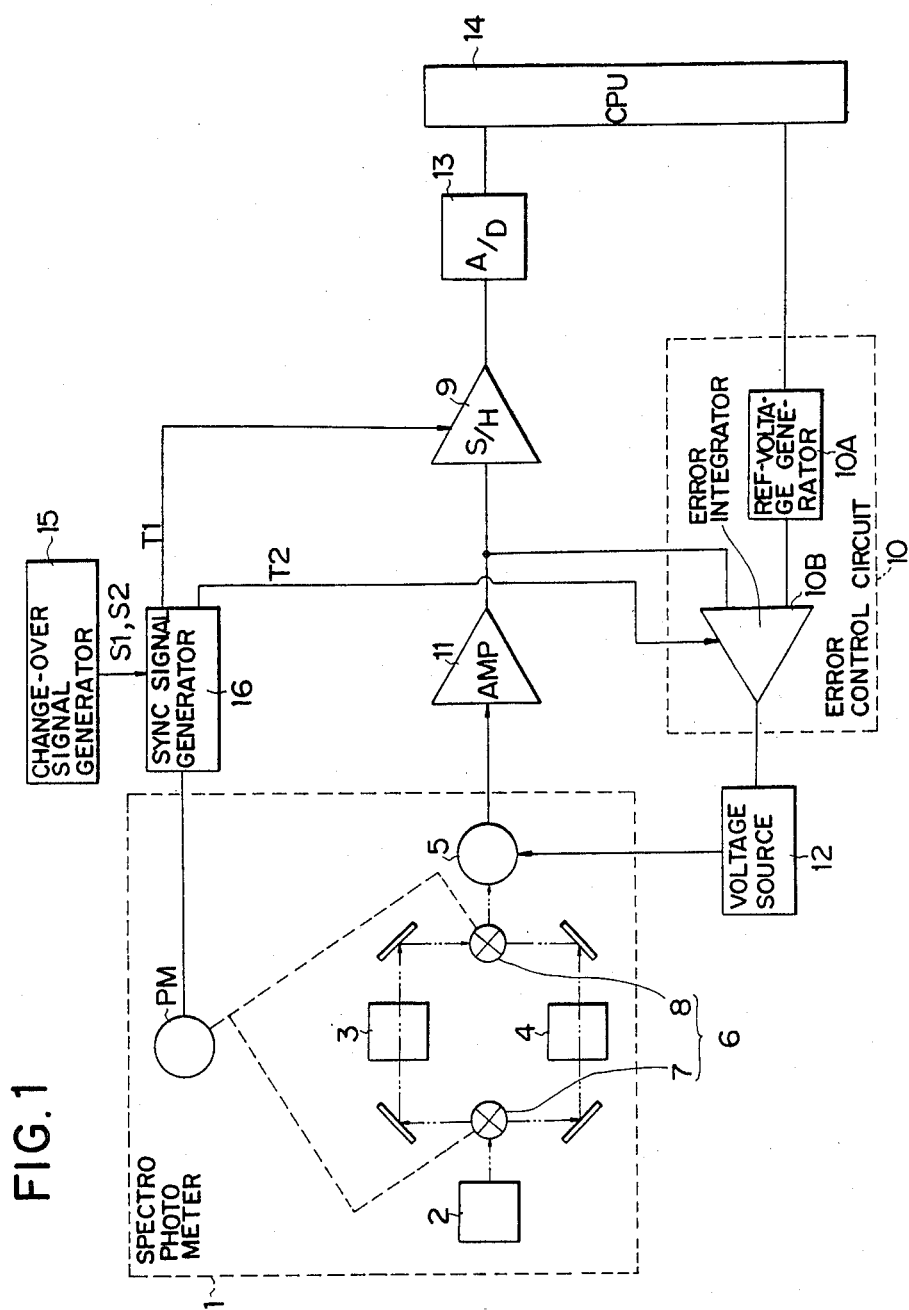
FIG. 1 is a block diagram of one embodiment of the measurement control apparatus of the invention associated with a spectrophotometer main section.
Figure 6:
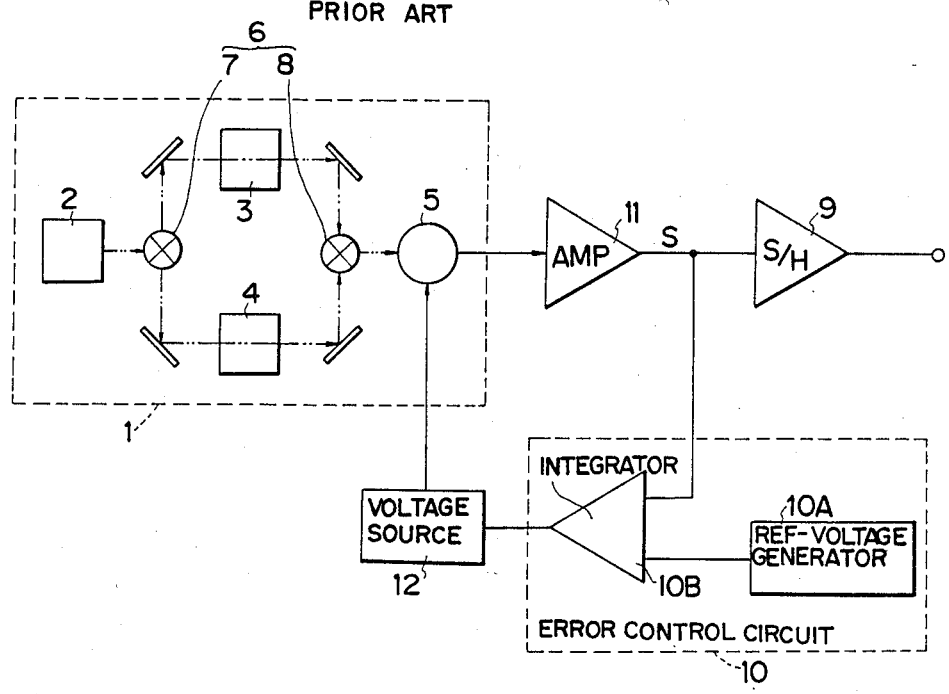
FIG. 6 is a block diagram of one example of the prior art spectrophotometer.
Figure 7:
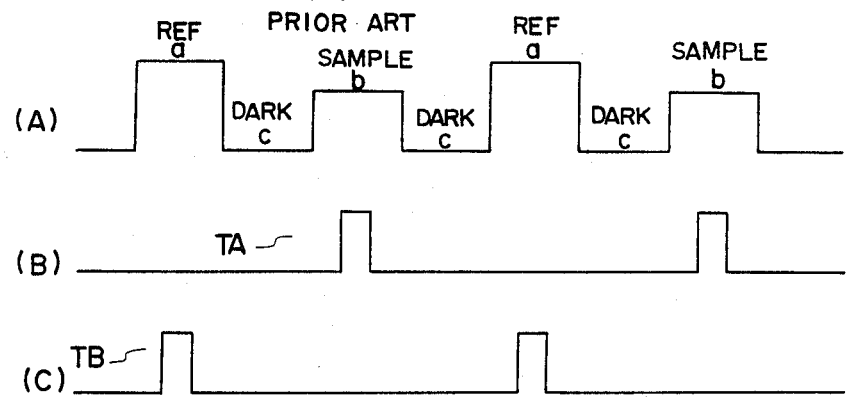
FIG. 7 is a time chart showing waveforms of signals appearing at various points in the spectrophotometer shown in FIG. 6.

Referring to FIG. 1, there is shown one embodiment of the measurement control apparatus of the invention with which the control method according to the first aspect of the invention may be carried out. Since a main section of the spectrophotometer shown in FIG. 1 is essentially the same as that of the prior art spectrophotometer shown in FIG. 6, and like numerals designate like parts in the figures, the organization and operation of the main section will be understood without further explanation. In FIG. 1, the sample/hold circuit 9 is electrically connected to a central processing unit or computer 14 through an analog/digital converter 13 so that an output of the sample/hold circuit 9 is supplied to the computer 14 in the form of a digital signal. The reference voltage generating circuit 10A is also electrically connected to the computer 14 so that an output voltage of the circuit 10A is controlled by a signal read out of the computer 14. The circuit shown in FIG. 1 further includes a preparatory scanning/measurement scanning change-over signal generating means 15 and a sync signal generating circuit 16 whose first input is connected to the change-over signal generating means 15 and second input is connected to a pulse motor PM for driving the beam path switching means 6, and whose first output is connected to the sample/hold circuit 9 and second output is connected to the synchronization error integrator circuit 10B. The preparatory scanning/measurement scanning changeover signal generating means 15 functions to selectively generate a signal S1 used for commanding the preparatory scanning and a signal S2 used for commanding the measurement scanning, and the sync signal generating circuit 16 funtions to generate, in synchronism with the operation of the beam path switching means 6, a first timing signal T1 for synchronously controlling the sample/hold circuit 9 and a second timing signal T2 for synchronously controlling the synchronization error integrator circuit 10B. The function of these components will become more apparent from the following description of measurement control according to the first aspect of the invention.

Figure 2:
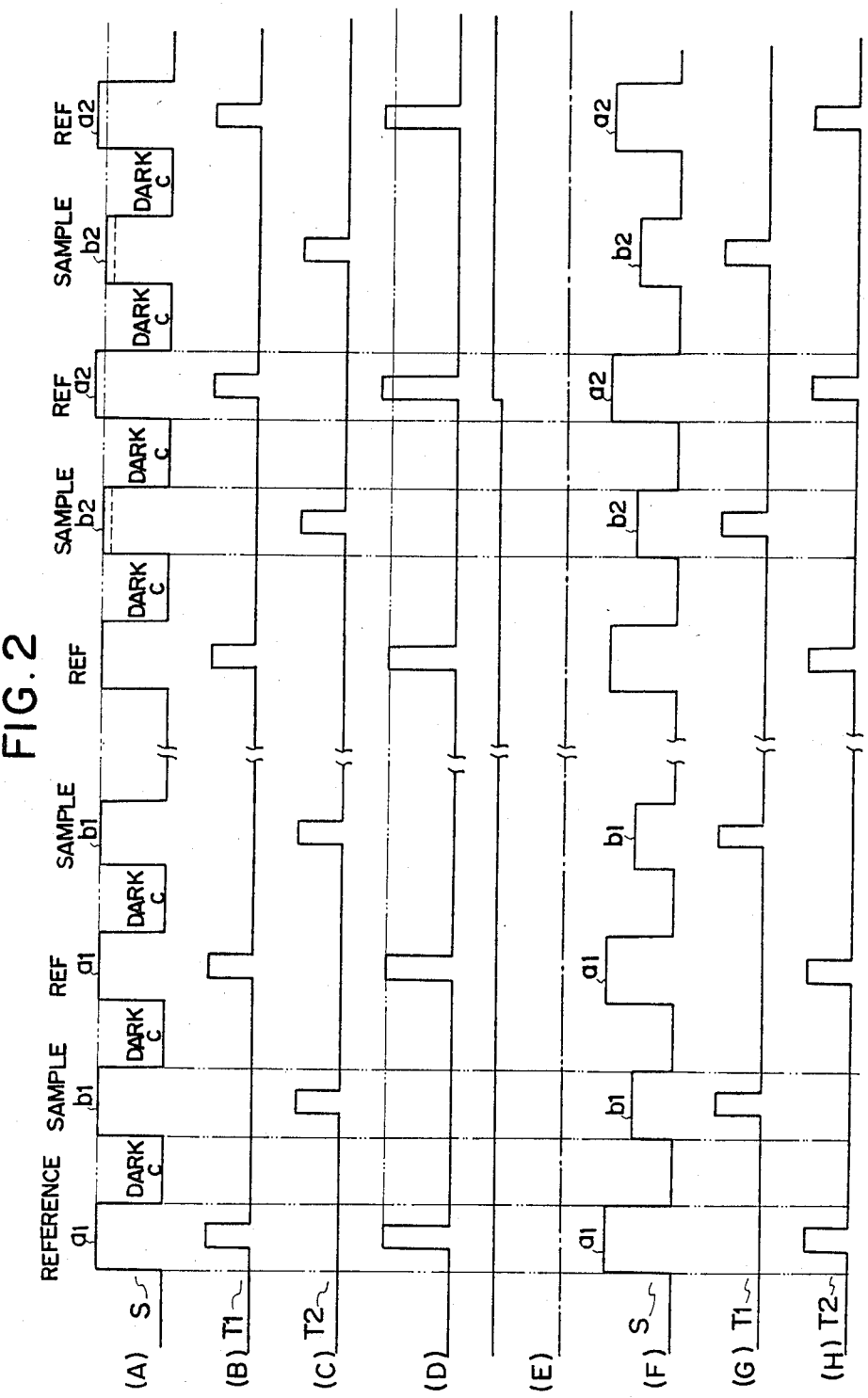
FIG. 2 is a time chart showing waveforms of signals appearing at various points in the apparatus shown in FIG. 1.

The measurement control method according to the invention includes a preparatory scanning stage prior to actual measurement of a sample material to be analyzed. In the preparatory scanning stage, the sample cell 3 is set to a substantially 100% transmittance state showing substantially no characteristic wavelength response (that is, the sample cell 3 is empty or filled with a standard material having substantially no charateristic spectral response and high transparency, for example). In this state, the sample cell 3 and the reference cell 4 are alternately scanned with radiation at each wavelength in the range over which measurements of a sample material are to be made. It is a matter of course that the reference cell 4 is also set to the same state as the sample cell 3, that is, a substantially 100% transmittance state in this preparatory scanning stage. The waveform of an output signal S produced by the photomultiplier or detector 5 during the preparatory scanning is shown in FIG. 2(A). It is to be noted that the waveform of an output signal of the amplifier 11 is substantially the same as that of the photomultiplier 5. In Fig.2(A), impulses a1 and a2 correspond to outputs of the photomultiplier 5 which responds to the reference beam (to be referred to as "reference output", hereinafter), and impulses b1 and b2 correspond to output of the photomultiplier 5 which responds to the sample beam (to be referred to as "sample output", hereinafter). The reference output impulses a1 and a2 are output impulses at different wavelengths, and the sample output impulses b1 and b2 are output impulses at the same wavelengths as the reference output impulses a1 and a2, respectively.

In this preparatory scanning stage, the preparatory scanning/measurement scanning change-over signal generating means 15 generates a preparatory signal S1 used for commanding the preparatory scanning when said change-over signal generating means 15 is actuated manually by the operator's switching-on or automatically in accordance with the preset program. Upon receipt of this preparatory signal S1, the sync signal generating circuit 16 produces a pulse as shown in FIG. 2(B) as a first timing signal T1 for synchronously controlling the sample/hold circuit 9, and a pulse as shown in FIG. 2(C) as a second timing signal T2 for synchronously controlling the synchronization error integrator circuit 10B. The circuit 16 is designed to generate first and second timing signals T1 and T2 in response to signals from the beam path switching devices 7 and 8 or the pulse motor PM for driving them. More specifically, in the preparatory scanning stage, the circuit 16 generates as the first timing signal T1 a pulse just within the duration when the beam is switched to follow the reference path passing the reference cell 4, that is, the duration of each reference output impulse a1 and a2, and as the second timing signal T2 a pulse just within the duration when the beam is switched to follow the sample path passing the sample cell 3, that is, the duration of each sample output impulse b1 and b2. Upon receipt of first timing signals T1, the sample/hold circuit 9 functions to sample and hold outputs of the amplifer 11 in synchronism with the timing signals. As shown in FIG. 2(D) the sample/hold circuit 9 functions to sample reference output impulses a1 and a2 from among the detector outputs as shown in FIG. 2(A), As a result, the sample/hold circuit 9 produces an output whose waveform is shown in FIG. 2(E). The A/D converter 13 converts this output into a digital signal which is stored in the computer 14. On the other hand, upon receipt of second timing signals T2 corresponding to sample output impulses b1 and b2, the synchronization error integrator circuit 10B functions to compare the level of a sample output impulse b1, b2 with the reference voltage to determine the difference between them and integrate the difference. (It should be noted that the reference voltage used in the preparatory scanning stage is generally a fixed voltage unlike the varying reference voltage used in actual sample measurement as will be described later.) The integrator circuit 10B produces an output voltage based on the integrated value, with which the output voltage of the high voltage source 12 is controlled so as to keep the sample output impulses b1 and b2 at a constant level. For example, even when there is the tendency that as compared with the sample output impulses b1 at one wavelength, the sample output impulses b2 at another wavelength are at a lower level as shown by the broken lines in FIG. 2(A), the sample output impulses b2 at the other wavelength are corrected to the same level as the sample output impulses b1 at the one wavelength as shown by the solid lines. On the other hand, the reference output impulses a1 and a2 are at different levels when the sample and reference beam paths in the spectrophotometer main section are different in wavelength response due to fogging of mirrors or the like. In the above-illustrated embodiment, for example, as compared with the reference output impulses a1 at one wavelength, the reference output impulses a2 at another wavelength are at a higher level in FIG. 2(A). As a result of this level increase, the corresponding output of the sample/hold circuit 9 is also increased to a higher level as shown in FIG. 2(E). In summary, in the preparatory scanning stage, the sample outputs are kept at a constant level whereas the reference outputs change their level with wavelength due to variations in spectral response of the sample and reference beam paths in the spectrophotometer main section 1 and accordingly, the sample/hold circuit 9 produces reference outputs varying with wavelength which are stored in the computer 14.

In the sample analysis or measurement scanning stage, measurements are made on a sample material to be analyzed by filling the sample cell 3 with the sample material, keeping the reference cell 4 at a substantially 100% transmittance state as in the preparatory scanning stage, and alternately scanning the sample and reference cells 3 and 4 with radiation of varying wavelengths. During this measurement, the preparatory scanning/measurement scanning change-over signal generating circuit 15 produces a measurement signal S2 used for commanding the measurement scanning said signal being fed to the sync signal generating circuit 16, which in turn, produces pulses as shown in FIG. 2(G) as the first timing signals T1 for synchronously controlling the sample/hold circuit 9 and pulses as shown in FIG. 2(H) as the second timing signals T2 for synchronously controlling the synchronization error integrator circuit 10B. In the measurement stage, as described in conjunction with the prior art spectrophotometer, the change-over signal generating circuit 15 produces as the first timing signal T1 a pulse just within the duration when the beam is switched to follow the sample path, that is, the duration of each sample output impulse b1 and b2, and as the second timing signal T2 a pulse just within the duration when the beam is switched to follow the reference path, that is, the duration of each reference output impulse a1 and a2. Upon receipt of first timing signals T1, the sample/hold circuit 9 functions to sample and hold in synchronism therewith sample output impulses b1 and b2 from among the outputs of the amplifier 11 appearing during measurement as shown in FIG. 2(F). The A/D converter 13 converts the outputs of the sample/hold circuit 9 into digital signals which are stored in the computer 14. In the measurement stage, for each wavelength, the computer 14 functions to read out a signal representative of the reference output level stored during the preparatory scanning and supply it to the reference voltage generating circuit 10A. As a result, the reference output level stored during the preparatory scanning or the corresponding voltage is supplied to the synchronization error integrator circuit 10B as a reference voltage. Upon receipt of second timing signals T2 corresponding to reference output impulses a1 and a2, the synchronization error integrator circuit 10B functions to compare a reference output impulse a1, a2 with the reference voltage to determine the difference between them and integrate the difference. The integrator circuit 10B produces an output voltage based on the integrated value, with which the output voltage of the high voltage source 12 is controlled to correct the level of a reference output impulse a1, a2 so as to be equal to the reference voltage.

In the preparatory scanning stage of the first control method according to the invention, the sample cell 3 is set to a state substantially free of characteristic spectral response (that is, the cell transmittance is substantially 100% at all wavelengths), sample outputs are made constant in said state, and corresponding reference outputs, that is, signals varying with the difference in spectral response between the sample and reference paths in the spectrophotometer main section 1 are stored in the computer 14. In the subsequent measurement stage, the reference output stored during the preparatory scanning is read out for each wavelength. Using the output level or the corresponding voltage as the reference voltage, control is made such that a reference output obtained in a measurement may be equal to this reference voltage. Accordingly, since reference outputs in measurements at all wavelengths correspond to the sample output levels resulting from the sample cell 3 set to a substantially 100% transmittance state, outputs (exactly, sample outputs) of the sample/hold circuit 9 always correctly represent the transmittance of the sample material at all wavelengths independent of the difference in spectral response between the sample and reference paths in the spectrophotometer main section 1. The sample outputs supplied to the computer 14 during the measurement operation may be properly processed for record or display purpose in a well-known manner.

Figure 3:
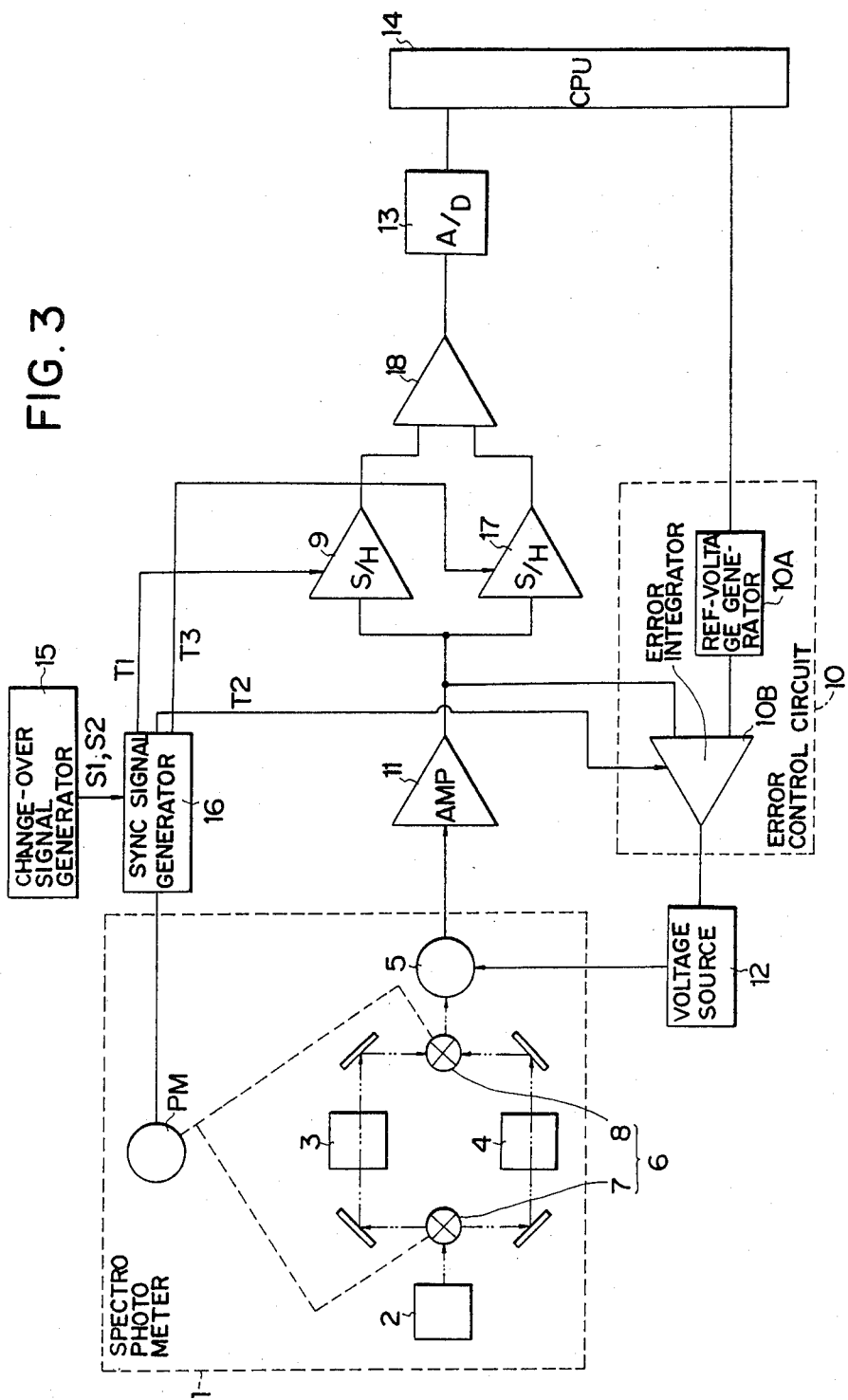
FIG. 3 is a block diagram of another embodiment of the measurement control apparatus of the invention.

FIG. 3 illustrates another embodiment of the measurement control apparatus with which the first control method according to the invention may be carried out. This circuit arrangement is different from that of FIG. 1 in that the output of the amplifier 11 is connected to first and second sample/hold circuits 9 and 17. The first and second sample/hold circuits 9 and 17 are also connected to the first and third outputs of the sync signal generating circuit 16 such that the first sample/hold circuit 9 operates in synchronism with first timing signals T1 as in the previous embodiment and the second sample/hold circuit 17 operates in synchronism with third timing signals T3 as will be described later. The outputs of both the sample/hold circuits 9 and 17 are supplied to an arithmetic circuit 18 which performs subtractive operation to determine the difference between outputs of the circuits 9 and 17. The difference output of the arithmetic circuit 18 is supplied to the computer 14 through the A/D converter 13.

The third timing signals T3 described above are produced by the sync signal generating circuit 16 as well as the first and second timing signals T1 and T2. The third timing signal T3 is a pulse signal developed just within the duration between one reference output impulse a1 or a2 and the adjoining sample output impulse b1 or b2, that is, a low level duration c as shown in the diagram of FIG. 2(A) or 2(F). Upon receipt of a third timing signal T3, the second sample/hold circuit 17 functions to sample and hold an output of the amplifier 11 developed within the duration when the beam path is being switched from one to the other cell in the spectrophotometer main section 1, that is, an output corresponding to the background radiation including dark current, and produces an output representative of the amplifier output level. Then, the arithmetic circuit 18 produces an output which is equal to an output (reference output or sample output) of the first sample/hold circuit 9 minus the background radiation level.

In the apparatus shown is FIG. 3, more accurate measurement is made because the influence of background radiation is eliminated.

Figure 4:
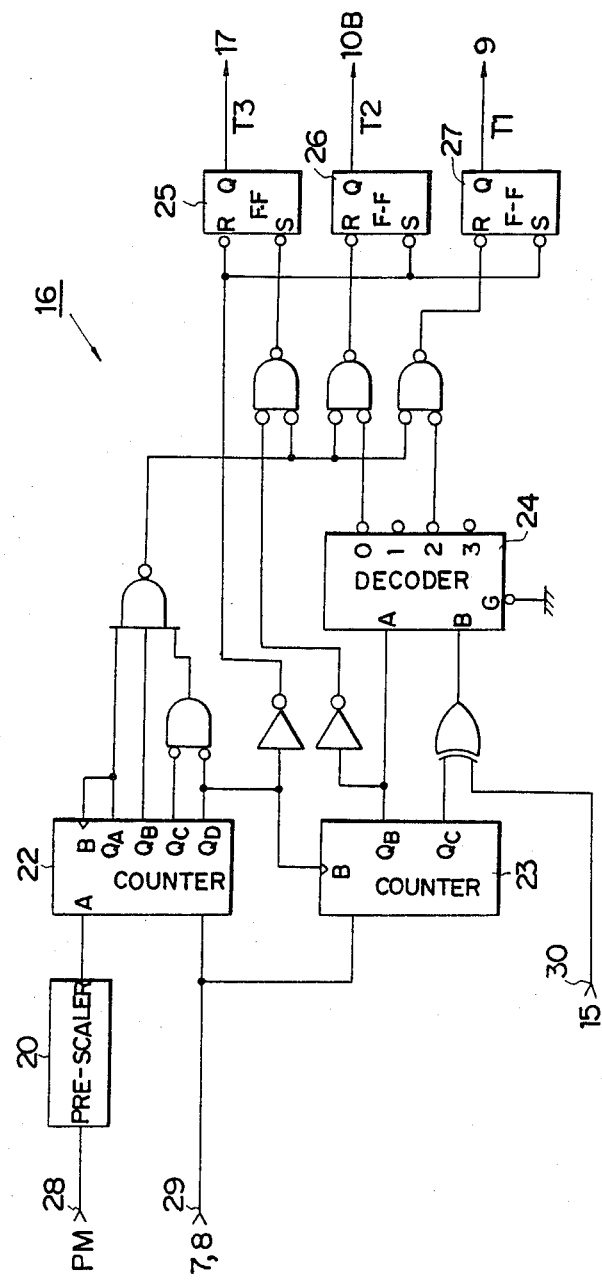
FIG. 4 is a block diagram of one example of a sync signal generating circuit used in the control apparatus of the invention.

FIG. 4 illustrates an example of the sync signal generating circuit 16. As seen from FIG. 4, the sync signal generating circuit 16 is composed of a pre-scaler 20, counters 22 and 23, a decoder 24, RS flip-flops 25, 26 and 27, and the like. The circuit 16 has a first input terminal 28 which receives a pulse from the pulse motor PM driving the beam path switching means 6, a second input terminal 29 which receives a sync signal PO from the beam path switching device 7 or 8 of the beam path switching means 6, that is, a pulse signal developed at the same period as the beam path switching, and a third input terminal 30 which receives a change-over signal SC from the preparatory scanning/measurement scanning change-over signal generating circuit 15 (which corresponds to the preparatory signal S1 or measurement signal S2). The flip-flops 25, 26 and 27 constitute outputs of this circuit 16. The flip-flops 25 develops third timing signals T3, the flip-flop 26 develops second timing signals T2, and the flip-flop 27 develops first timing signals T1.

Figure 5A:
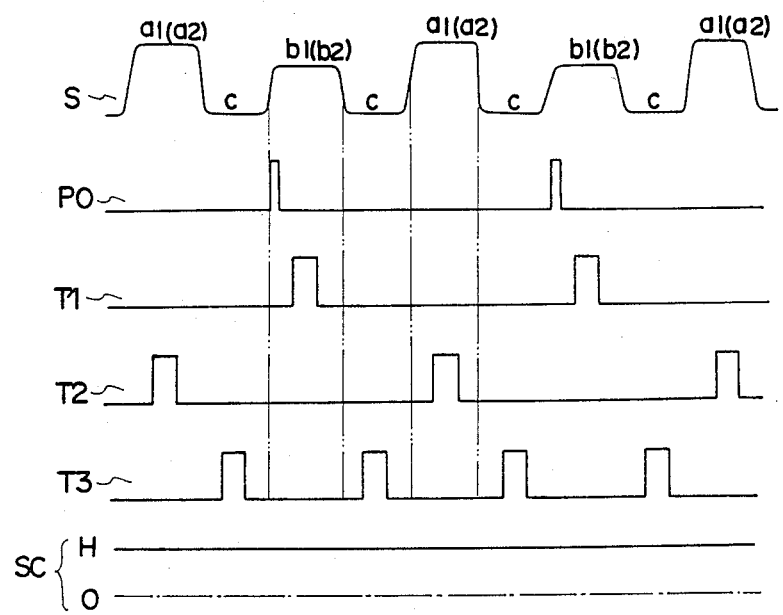
FIGS. 5A and 5B are time charts showing waveforms of signals appearing at various points in the circuit shown in FIG. 4.
Figure 5B:
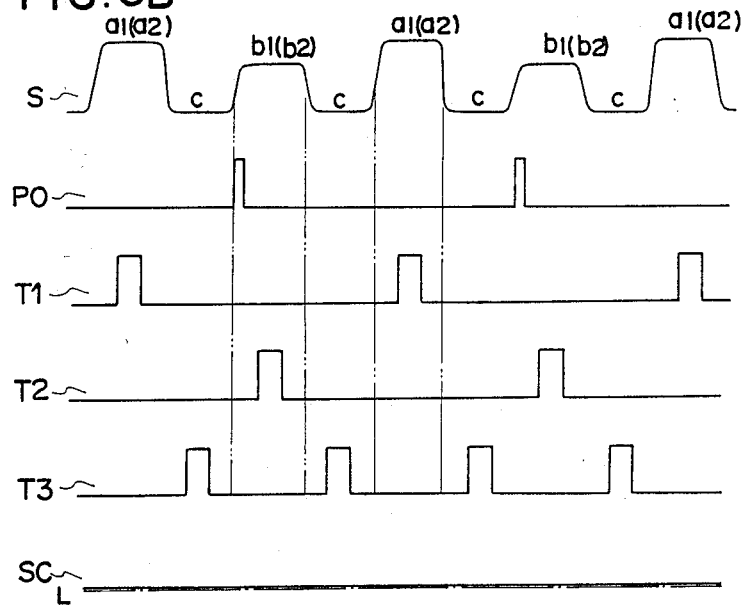

The input signals PO and SC and the output signals (timing signals) T1, T2 and T3 of the sync signal generating circuit 16 of FIG. 4 are shown in FIGS. 5A and 5B together with the output signal S of the amplifier 11. FIGS 5A and 5B show the waveforms of various signals in the preparatory scanning and measurement stages, respectively. The changeover signal SC is at a high level H during the preparatory scanning and at a low level L during the measurement, and the timing of generating the first and second timing signals T1 and T2 is determined by the level of the change-over signal SC. In order to avoid the influence of fluctuating or rounded rising and falling edges of the reference and sample output impulses appearing as output signals S of the amplifier 11, the sync signal generating circuit 16 is designed such that each of the timing signals T1, T2 and T3 may be developed in a central flat portin of the reference output duration, sample output duration and background radiation duration, respectively.

Next, the measurement control method according to a second aspect of the invention will be described. As in the first control method according to the invention, the preparatory scanning is carrried out prior to the actual measurement of a sample material to be analyzed, in which the sample cell is set to a substantially 100% transmittance state, and in this state the sample and reference cells 3 and 4 are scanned with radiation of each wavelength in the range at which measurements of the sample material are made. However, in the preparatory scanning stage of the second control method according to the invention, feedback control is made such that reference outputs may be equal to the reference voltage (which is a fixed voltage in the preparatory scanning stage) and hence, a fixed voltage, and sample outputs are stored in the computer 14, as done in the sample measurement procedure. More specifically, in the preparatory scanning stage, pulses corresponding to sample output impulses b1 and b2 as shown in FIG. 2(G) are used as the first timing signals T1 for synchronizing the sample/hold circuit 9, and pulses corresponding reference output impulses a1 and a2 as shown in FIG. 2(H) are used as the second timing signals T2 to be applied to the synchronization error integrator circuit 10B as done in the sample measurement procedure. The sample outputs stored in the computer 14 will vary with wavelength if the sample and beam paths in the spectrophotometer main section are different in wavelength response. Differently stated, the reciprocal of a sample output stored in this preparatory scanning stage corresponds to a reference output stored in the preparatory scanning stage in the first control method. In the subsequent measurement stage, the reciprocal of a sample output stored in the preparatory scanning stage multiplied by a standard voltage (fixed voltage) is used as a reference voltage, and feedback control is made such that a reference output may be equal to this reference voltage. Of course, the first and second timing signals T1 and T2 used in the measurement stage are the same as those used in the preparatory scanning stage, that is, those used in the measurement state of the first method. It will thus be understood that the second method need not change over the first and second timing signals T1 and T2 between the preparatory scanning and the measurement stages.

Since in the measurement stage of the second control method, a reference output is equal to the level of a sample output resulting from the sample cell 3 set to a substantially 100% transmittance state as in the first control method, an output (sample output) of the sample/hold circuit 9 produced during a measurement always correctly represents the transmittance of a sample material at all wavelengths independent of a difference in spectral response between the sample and reference beam paths in the spectrophotometer, if any.

In the practice of the second control method, a stored sample output may be converted into its reciprocal by means of the computer itself, and no particular change is necessary for the illustrated apparatus to carry out the second control method. Of course, a reciprocal converter circuit may be added to the illustrated circuitry. Alternatively, the detected sample output may be converted into its reciprocal for storage in the preparatory scanning stage and the stored reciprocal may be read out in the measurement stage. The reference voltage generating circuit 10A may be provided with a function of multiplying said reciprocal by a standard voltage.

In the above-mentioned embodiment of the first control method, the so-called dynode feedback control system is used in which the voltage to the photomultiplier 5 is controlled in a feedback manner such that sample outputs developed in the preparatory scanning stage and reference outputs developed in the measurement stage may be equal to the reference voltage. However, in other embodiments wherein the photomultiplier is replaced by another radiation detector such as a photo diode, photo transistor, photo cell, photoconductive cell, etc., and an amplifier whose gain is controllable may be used to amplify the output of the radiation detector. Then, the gain of the amplifier is controlled in a feedback manner such that reference or sample outputs may be equal to the reference voltage. The error control circuit 10 may be modified so as to meet this control system.

As understood from the foregoing description, according to the first and second control methods of the invention, even when the sample beam path passing the sample cell 3 and the reference beam path passing the reference cell 4 in the spectrophotometer main section are not precisely identical in spectral response due to fogging of mirrors in the paths or the like, an output of the spectrophotometer developed in the measurement of a sample material correctly represents the transmittance of the sample material at all wavelengths. This leads to the advantages that the precision of spectroscopic analysis is significantly increased over the prior art, and the need for adjusting operations as by the operator's manual adjustment is eliminated. The apparatus of the invention allows such high precision measurement to be made in an easy and simple manner.

What we claim is:

1. In a spectrophotometer of the type wherein monochromatic radiation of varying wavelengths is alternately directed to a reference cell having a transmittance of substantially 100% and a sample cell containing a sample to be analyzed to form reference and sample beams, the reference beam and the sample beam are detected for each wavelength by means of radiation detector means which produces an electrical output, and an output of said detector means which responds to the reference beam is fed back to said detector means such that said output may be equal to a reference voltage upon measurement of the sample at all wavelengths, thereby controlling the gain of said detector means, whereby in output of said detector means which responds to the sample beam represents the transmittance of the sample for each wavelength, a method for controlling the measurement, comprising a preparatory scanning stage including setting both the reference and sample cells to a substantially 100% transmittance state, scanning the reference and sample cells with radiation of each wavelength at which measurement is to be made in said state, feeding back an output of the detector means which responds to the sample beam during said scanning to said detector means such that the detector output responding to the sample beam may become constant at all wavelengths, thereby controlling the gain of said detector means, and storing an output of said detector means which responds to the reference beam during said scanning, and a sample analyzing stage in which using the stored output for each wavelength of said detector means which has responded to the reference beam during said preparatory scanning or the corresponding voltage as a reference voltage, said detector means is controlled upon measurement of the sample sucn that an output of said detector means which responds to the reference beam may be equal to said reference voltage.

2. The control method as set forth in claim 1 wherein said detector means consists of a photo detector and an amplifier connnected thereto.

3. The control method as set forth in claim 2 wherein said photo detector is a photomuliplier whose gain is controlled in a feedback manner.

4. The control method as set forth in claim 2 wherein said photo detector is selected from the group consisting of a photo diode, photo transistor, photo cell and photoconductive cell, and the gain of the amplifier connected to said photo detector is controlled in a feedback manner.

5. In a spectrophotometer of the type wherein monochromatic radiation of varying wavelengths is alternately directed to a reference cell having a transmittance of substantially 100% and a sample cell containing a sample to be analyzed to form reference and sample beams, the reference beam and the sample beam are detected for each wavelength by means of radiation detector means which produces an electrical output, and an output of said detector means which responds to the reference beam is fed back to said detector means such that said output may be equal to a reference voltage upon measurement of the sample at all wavelengths, thereby controlling the gain of said detector means, whereby an output of said detector means which responds to the sample beam represents the transmittance of the sample for each wavelength, a method for controlling the measurement, comprising a preparatory scanning stage including setting both the reference and sample cells to a substantially 100% transmittance state, scanning the reference and sample cells with radiation of each wavelength at which measurement is to be made in said state, feeding back an output of the detector means which responds to the reference beam during said scanning to said detector means such that the detector output responding to the reference beam may become constant at all wavelengths, thereby controlling the gain of said detector means, and storing an output of said detector means which responds to the sample beam during said scanning or its reciprocal, and a sample analyzing stage in which using the reciprocal of the output stored for each wavelength of said detector means which has responded to the sample beam during said preparatory scanning multiplied by a standard voltage as a reference voltage, said detector means is controlled upon measurement of the sample such that an output of said detector means which responds to the reference beam may be equal to said reference voltage.

6. The control method as set forth in claim 5 wherein said detector means consists of a photo detector and an amplifier connected thereto.

7. The control method as set forth in claim 6 wherein said photo detector is a photomultiplier whose gain is controlled in a feedback manner.

8. The control method as set forth in claim 6 wherein said photo detector is selected from the group consisting of a photo diode, photo transistor, photo cell and photoconductive cell, and the gain of the amplifier connected to said photo detector is controlled in a feedback manner.

9. In a spectrophotometer comprising a radiation source capable of emitting monochromatic radiation of varying wavelengths, a reference cell, a sample cell, radiation detector means which produces an electrical output, and a beam path switching means for directing monochromatic radiation of varying wavelengths from the source alternately to the reference and sample cells to form reference and sample beams and directing in synchronism the reference beam and the sample beam to said detector means, an apparatus for controlling the measurement comprising a sample/hold circuit for sampling an output of said detector means in synchronism with a first timing signal, a computer having a function of storing an output of said sample/hold circuit and reading out the data stored, a reference voltage generating circuit for generating a reference voltage corresponding to the output signal of said sample/hold circuit previously stored in said computer, an error control circuit for comparing the output of said detector means with the reference voltage in synchronism with a second timing signal and controlling in accordance with the difference the gain of said detector means, and a sync signal generating circuit for generating said first and second timing signals in response to the switching of said beam path switching means, wherein said sync signal generating circuit is switched between a first state in which said circuit generates as the first timing signal a signal within a duration when said detector means is producing an output by detecting the reference beam, and as the second timing signal a signal within a duration when said detector means is producing an output by detecting the sample beam, and a second state in which said circuit generates as the first timing signal a signal within a duration when said detector means is producing an output by detecting the sample beam, and as the second timing signal a signal within a duration when said detector means is producing an output by detecting the reference beam.

10. The control apparatus as set forth in claim 9 wherein said detector means consists of a photo detector and an amplifier connected to said photo detector for amplifying an output thereof.

11. The control apparatus as set forth in claim 10 wherein said photo detector is a photomultiplier whose gain is controlled in a feedback manner.

* * * * *